United States Patent [19]

Ohta et al.

[11] 4,443,781

[45] Apr. 17, 1984

[54] GAS DETECTING SENSOR

[75] Inventors: Minoru Ohta; Yutaka Hattori, both of Okazaki; Tomio Kawakami, Nishio; Michitosi Onoda, Toyohashi, all of Japan

[73] Assignee: Nippon Soken, Inc., Nishio, Japan

[21] Appl. No.: 336,401

[22] Filed: Dec. 31, 1981

[30] Foreign Application Priority Data

Apr. 27, 1981 [JP] Japan .................................. 56-63626

[51] Int. Cl.³ ............................................. H01L 7/00
[52] U.S. Cl. .................................... 338/34; 73/27 R; 422/98
[58] Field of Search ................... 338/34, 35; 73/27 R; 422/98; 340/632–634

[56] References Cited

U.S. PATENT DOCUMENTS

| | | | |
|---|---|---|---|
| 3,933,028 | 1/1976 | Laud et al. ........................ | 338/34 X |
| 4,007,435 | 2/1977 | Tien ..................................... | 338/34 |
| 4,012,709 | 3/1977 | Logothetis et al. .................. | 338/34 |
| 4,314,996 | 2/1982 | Sekado et al. ..................... | 338/34 X |
| 4,333,067 | 6/1982 | Kugimiya et al. .................... | 338/34 |
| 4,338,281 | 7/1982 | Treitinger ......................... | 338/34 X |

Primary Examiner—C. L. Albritton
Attorney, Agent, or Firm—Cushman, Darby & Cushman

[57] ABSTRACT

A compact and durable gas detecting sensor for detecting the partial pressure of oxygen gas in the exhaust gases of an internal combustion engine is disclosed. The sensor is provided with a sensing element made of ceramic material having an electrical characteristic which varies in response to variations in the partial pressure of oxygen gas, such as CoO, a base member made of electrically insulating ceramic material, such as alumina, and electrodes held by the base member. The sensing element is integrally fixed to the base member through an intermediate layer made of ceramic material which is non-reactive with the sensing element.

10 Claims, 6 Drawing Figures

GAS DETECTING SENSOR

BACKGROUND OF THE INVENTION

The present invention relates to a gas detecting sensor for detecting the partial pressure of oxygen gas contained within exgaust gases discharged from an internal combustion engine and for measuring air/fuel ratio of the combustion mixture to be supplied into the internal combustion engine.

Recently, the so-called "lean burn system" that is, the system of operating an internal combustion engine with an air/fuel ratio larger than the stoichiometric value thereof, in order to reduce harmful components contained within the exhaust gases and lower the fuel consumption, has been proposed.

The above described "lean burn system" requires a detecting means for accurately detecting the air/fuel ratio in a range of lean mixtures.

U.S. Pat. No. 3,933,028 and U.S. Pat. No. 4,012,709 show examples of such a detecting sensor as described above.

These detecting sensors are provided with a sensing element made of cobalt monoxide (CoO) or an alloy of cobalt monoxide (CoO) and magnesium monoxide (MgO). These detecting sensors are further provided with a heating means for heating and maintaining the sensing element at a predetermined temperature, for example 900° C. in order to prevent cobalt monoxide from changing into tricobalt tetroxide ($Co_3O_4$) and to compensate for any output fluctuation caused by the temperature change.

These conventional detecting sensors have a problem in that the size of the sensing element becomes large.

In order to solve the problem of the conventional detecting sensor, the present inventors have discovered a sensor wherein on a base plate made of a material containing alumina ($Al_2O_3$) as a main ingredient, a film shaped sensing element and film shaped electrodes are formed.

However, the present inventors have found another problem in the sensor having the above described structure.

Namely, when the device provided with the sensing element made of CoO and the base plate made of alumina is heated, the reaction of $CoO + Al_2O_3 \rightarrow CoAl_2O_4$ occurs at about 950° C., so that CoO of the sensing element is changed into $CoAl_2O_4$.

On the other hand, since the phase of CoO is changed into $Co_3O_4$ in an oxidizing atmosphere, the sensing element made of CoO must be maintained at a temperature above 900° to 950° C. in order to prevent such a phase change of the CoO.

However, at such a high temperature, CoO reacts on alumina gradually changing it into $CoAl_2O_4$, consequently, the sensing element made of CoO loses its function.

Furthermore, as described above, the sensing element and the base plate cannot be sintered at a high temperature. Therefore, a sufficiently high adhering strength of the sensing element to the base plate cannot be obtained.

The sensing element for detecting the partial pressure of oxygen gas contained within the exhaust gases in fuel lean combustion can be also made of nickel monoxide, a perovskite type double oxide a expressed $ABO_3$, wherein A contains lanthanum and/or B contains a cobalt other than cobalt oxide monoxide.

The present inventors have also found that the sensor provided with the sensing elements made of this material have the same problem as that provided with the sensing element made of cobalt monoxide.

Accordingly, one object of the present invention is to provide a durable gas detecting sensor of which the sensing element does not react on the material of the base plate member to cause a phase change at a high temperature.

Another object of the present invention is to provide a compact gas detecting sensor wherein a film shaped sensing element is formed on a plate shaped base plate member.

Still another object of the present invention is to provide a gas detecting sensor wherein the sensing element and the base plate member are integrally sintered through a substantially non-reactive material.

DESCRIPTION OF THE DRAWINGS

Other objects and advantages of the invention will become apparent from the following description of embodiments of the invention with reference to the accompanying drawings wherein.

SUMMARY OF THE INVENTION

Figure 1:
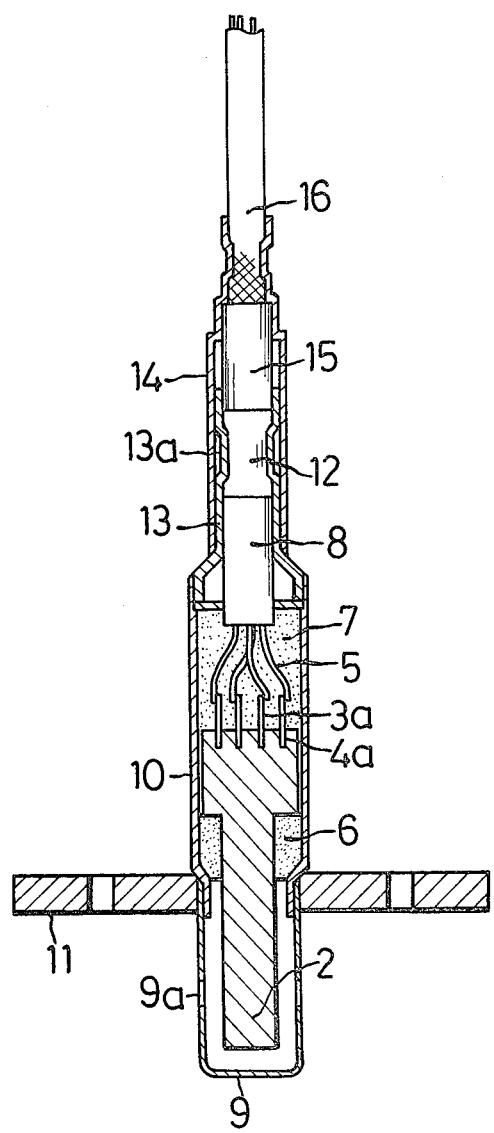
FIG. 1 is a sectional view of a gas detecting device wherein a gas detecting sensor of one embodiment of the present invention is accomodated.
Figure 2:
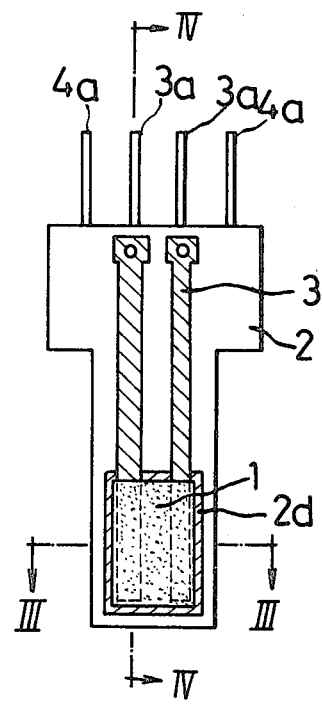
FIG. 2 is a front view of one part of FIG. 1.
Figure 3:
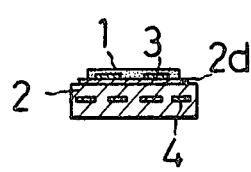
FIG. 3 is a sectional view taken along the line III—III of FIG. 2.
Figure 4:
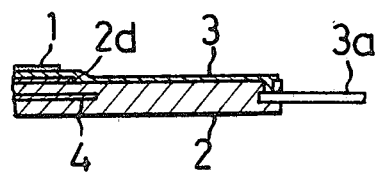
FIG. 4 is an enlarged view of the section taken along the line IV—IV of FIG. 2.

The gas detecting sensor of the present invention is provided with a base member made of ceramic material such as $Al_2O_3$, a sensing element made of ceramic material of which the electrical resistance changes in response to the partial pressure of oxygen gas, and a pair of electrodes. The electrodes are integrally formed on one surface of the base member, the sensing element is in contact with the electrodes and is joined to the base member through an intermediate layer made of a material which is non-reactive on the sensing element such as spinel.

DETAILED DESCRIPTION OF THE INVENTION

Hereinafter, the present invention will be explained in accordance with embodiments with reference to accompanying drawings.

In FIGS. 1 to 4, a sensing element 1 made of cobalt monoxide is formed on one surface of a base body 2 so as to cover one portion of a pair of electrodes 3 by adhering cobalt monoxide paste to the surface of the base body 2 like a film and sintering together.

The cobalt monoxide paste is adhered to the base body 2 by a screen printing method, spraying method or the like.

The electrodes 3 are made of platinum, platinum-rhodium alloy or the like and are formed on the surface of the base body 2 like a film parallel to each other at a predetermined interval.

The base body 2 is made of alumina and formed into a plate shape. Within the base body 2, a heater 4 is embedded. The heater 4 is made of metal such as platinum, platinum-rhodium alloy, tungsten or molybudenum-manganese alloy, and is formed like a film.

To the top end of the base body 2, lead wires 3a and 4a are fixed and each lead wire is electrically connected to the electrodes 3 or the heater 4. Between the sensing element 1 and the base body 2, an intermediate layer 2d made of spinel ($MgAl_2O_4$) is formed. To each end of the lead wires 3a and 4a, sub-lead wires 5, made of a heat resistant metal such as stainless steel, are connected.

The base body 2 is accomodated within a protecting cover member 9 made of heat resistant metal and provided with holes 9a for introducing exhaust gases therein, and a pipe member 10 is connected to the cover member 9. In the connecting portion of the protecting cover member 9 and pipe member 10, a flange member 11 for fixing the cover member 9 and the pipe member 10 to an exhaust pipe (not shown) is mounted.

The base body 2 is supported by a retaining member 6 made of a sintered body such as alumina within the pipe member 10. And the top portion of the base body 2, the lead wires 3a and 4a and the sub-lead wires 5 are fixed within the pipe member 10 by means of inorganic binding agent 7.

To the pipe member 10, pipe members 13 and 14, are connected in order. Within the pipe members 13 and 14, an insulating pipe 8 made of alumina or the like, a bushing 12 made of fluorine-contained rubber or the like and a heat resistant rubber member 15 made of silicon rubber or the like are accomodated and the sub-lead wires 5 are inserted therethrough and extend outside the pipe member 14 and are covered by a covering member 16.

Hereinafter the method of producing the gas detecting sensor of the present invention will be explained.

Figure 5:
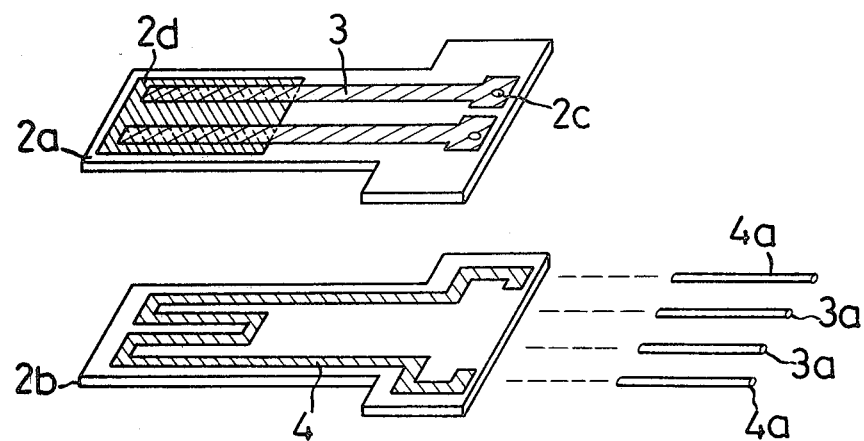
FIG. 5 is an exploded perspective view showing the assembling state of the parts of FIG. 2.

At first, thin plates 2a and 2b having a predetermined shape and size as shown in FIG. 5 are prepared by punching an alumina green sheet. Next, the paste of spinel ($MgAl_2O_4$) having the appropriate viscosity is adhered to one end portion of the upper surface of the thin plate 2a by screen printing to form the intermediate layer 2d.

After drying the formed intermediate layer 2d, a pair of electrodes 3 are printed on the thin plate 2a so that one end of each electrode covers the intermediate layer 2d while the other end thereof covers each of through holes 2c which are formed in the thin plate 2a.

On the upper surface of the thin plate 2b, the heater layer 4 is printed in the same manner as the electrodes 3.

Next, one end of each lead wire 4a is laid on the end of the heater layer 4 formed on the thin plate 2b and one end of each lead wire 3a is disposed so as to be opposed to each through hole 2c which is formed in the thin plate 2a. The thin plates 2a and 2b are combined so that the lower surface of the thin plate 2a is joined with the upper surface of the thin plate 2b while applying heat and pressure. Then, the paste of the same material as that of the electrode 3 is filled within the through holes 2c in order to firmly connect the lead wires 3a to the electrodes 3. Next, the combined body is heated within an electric furnace at a temperature from 1500° to 1600° C. in an air atmosphere for 3 hours.

The thin plates 2a and 2b are sintered to be integrally combined and the film shaped heater 4 is formed within the combined body.

As a result, the lead wires 3a and 4a are firmly adhered to the thin plates 2a and 2b due to the shrinkage of the thin plates 2a and 2b during the sintering step.

Next, the paste of cobalt monoxide of which the viscosity is appropriately adjusted is screen printed on the upper surface of the thin plate 2a so as to cover the layer 2d of spinel ($MgAl_2O_4$) and one portion of the electrodes. After being dried, the covered combined body is sintered in an air atmosphere at about 1150° C. for about 2 hours.

Since spinel ($MgAl_2O_4$) of the intermediate layer 2d has excellent heat resistance and electrically insulating properties, and scarcely reacts on the CoO of the sensing element 1 at 1150° C., the CoO of the sensing element 1 can be prevented from reacting on the alumina of the base body 2 to be changed into $CoAl_2O_4$.

Therefore, even after being used at a high temperature above 950° C., performance of the sensing element 1 is hardly lowered. The sensing element 1 of the present invention can be sintered together with the base body 2 at a high temperature in order to improve the strength thereof.

Figure 6:
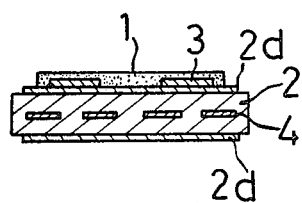
FIG. 6 is a sectional view showing another embodiment of the present invention.

FIG. 6 is a sectional view of a gas detecting sensor of another embodiment of the present invention.

In this embodiment, the intermediate layer 2d is provided on each of the upper and the lower surfaces of the base body 2 in order to reduce the warp of the base body 2, occurring during the sintering step.

This structure is particularly effective when the base body 2 is formed from a green sheet.

The double oxide expressed by $ABO_3$ for use as the material of the sensing element of the gas detecting sensor of the present invention can be preferably selected from the group of $LaCoO_3$, $LaMnO_3$, $La_{0.8}Sr_{0.2}CoO_3$, $LaNiO_3$, $La_{0.3}Co_{0.2}CoO_3$, $SrNb_{0.8}Co_{0.7}O_3$ and the like in addition to those described in the embodiments of the present invention.

And the material of the sensing element can be also prepared by dissolving MgO, CaO or the like of the solid phase into NiO or CoO.

The intermediate layer can be formed of cordierite, mullite, titania, zirconia or the like in place of spinel($MgAl_2O_4$).

As described above, the gas detecting sensor of the present invention is provided with a base plate member made of the material containing alumina as a main ingredient, and an intermediate layer which is formed between the base plate member and the sensing element.

Since the intermediate layer is made of a material that is substantially non-reactive with the sensing element, the sensing element is prevented from reacting with the alumina of the base plate member even if the gas detecting sensor of the present invention is used at a high temperature.

As a result, the performance of the gas detecting sensor is scarcely lowered.

Also the sensing element and the base plate member can be sintered together at a high temperature so that the strength the sensing element is adhered to the base plate member can be increased. Consequently, the sensing element can hardly be peeled off from the base plate member when the gas detecting sensor of the present invention is used under severe conditions.

Having now fully described the invention, it will be apparent to one of ordinary skill in the art that many changes and modifications can be made thereto without departing from the spirit of scope of the invention as set forth herein.

What is claimed is:

1. A gas detecting sensor for detecting the partial pressure of oxygen gas contained in exhaust gases, comprising:
   a base member made of ceramic material containing alumina as a main ingredient;
   a pair of electrodes held by said base member;
   a sensing element held by and fixed to said base member and electrically connected to said pair of electrodes; and sensing element having an electrical characteristic responsive to the partial pressure of oxygen gas, said sensing element being made of ceramic material selected from the group consisting of cobalt monoxide, nickel monoxide and perovskite-type double oxide which contains at least one of lanthanum and cobalt; and
   an intermediate layer of ceramic material which is substantially non-reactive with said sensing element, said intermediate layer being disposed between and separating said base member from said sensing element.

2. A gas detecting sensor according to claim 1, wherein:
   said electrodes are made of a material selected from the group consisting of platinum and a platinum-rhodium alloy.

3. A gas detecting sensor according to claim 1, wherein:
   said perovskite-type double oxide is selected from the group consisting of $CaCoO_3$, $LaMnO_3$, $La_{0.8}Sr_{0.2}CoO_3$, $LaNiO_3$ and $SrNb_{0.8}Co_{0.7}O_3$.

4. A gas detecting sensor according to claim 1, wherein:
   said ceramic material of said intermediate layer is selected from the group consisting of spinel, zirconia, cordierite, mullite and titania.

5. A gas detecting sensor according to claim 1, further comprising:
   a heating member which is embedded within and is surrounded by said base member, said heating member adapted for heating and maintaining said sensing element at a predetermined temperature.

6. A gas detecting sensor according to claim 5, wherein:
   said heating member is made of a material selected from the group consisting of platinum, platinum-rhodium alloy, tungsten and a molybudenum-manganese alloy.

7. A gas detecting sensor according to claim 1, wherein:
   said base member is a flat plate;
   each of said pairs of electrodes and said sensing element are film-shaped; and
   said sensing element is formed on the surface of said plate-shaped base member so as to cover at least a portion of each electrode.

8. A gas detecting sensor according to claim 7, wherein:
   said flat base member, said sensing element, said intermediate layer and said electrodes are integrally sintered.

9. A gas detecting sensor according to claim 7, wherein:
   said intermediate layer is formed on one portion of said plate-shaped base member;
   said pair of electrodes are formed on said plate-shaped base member at a predetermined interval so that one portion thereof is formed on said intermediate layer; and
   said sensing element is formed on said plate-shaped base member so as to cover said one portion of said electrodes and said intermediate layer.

10. A gas detecting sensor according to claim 7, further comprising:
    a film shaped heating member embedded within said base member for heating and maintaining said sensing element at a predetermined temperature; wherein said plate-shaped base member is composed of an upper thin plate and a lower thin plate which are integrally combined with each other;
    on the upper surface of said upper thin plate, said intermediate layer and one pair of said electrodes are printed so that said electrodes are formed at a predetermined interval and that one portion of each of said electrodes covers said intermediate layer and said sensing element is printed so as to cover said intermediate member and said one portion of said electrodes;
    said film shaped heating member is printed on the upper surface of said lower thin plate; and
    said upper thin plate on which said intermediate layer, said electrodes and said sensing element are formed, and said lower thin plate on which said heating member is formed, are combined by putting said upper thin plate on said lower thin plate and sintering together.

* * * * *